(12) United States Patent
Gabriel et al.

(10) Patent No.: US 9,999,942 B2
(45) Date of Patent: Jun. 19, 2018

(54) ENCLOSURE FOR LASER CUTTING OF HUMAN TISSUE

(71) Applicant: ALLOSOURCE, Centennial, CO (US)

(72) Inventors: Meghan Gabriel, Denver, CO (US);
Raymond Klein, Centennial, CO (US)

(73) Assignee: Allosource, Centennial, CO (US)

( * ) Notice: Subject to any disclaimer, the term of this patent is extended or adjusted under 35 U.S.C. 154(b) by 413 days.

(21) Appl. No.: 14/941,275

(22) Filed: Nov. 13, 2015

(65) Prior Publication Data

US 2016/0144454 A1    May 26, 2016

Related U.S. Application Data

(60) Provisional application No. 62/082,755, filed on Nov. 21, 2014.

(51) Int. Cl.

| | |
|---|---|
| *G01N 1/00* | (2006.01) |
| *B23K 26/12* | (2014.01) |
| *B23K 26/38* | (2014.01) |
| *G02B 5/20* | (2006.01) |
| *A61B 18/20* | (2006.01) |

(52) U.S. Cl.
CPC ............ *B23K 26/127* (2013.01); *B23K 26/38* (2013.01); *A61B 18/20* (2013.01); *G02B 5/208* (2013.01)

(58) Field of Classification Search
CPC ........................................................ A61L 2/20
See application file for complete search history.

(56) References Cited

U.S. PATENT DOCUMENTS

| | | |
|---|---|---|
| 5,429,810 A | 7/1995 | Knaepler et al. |
| 6,380,149 B2 | 4/2002 | Flynn et al. |
| 2011/0281352 A1 | 11/2011 | Raeder et al. |
| 2012/0177615 A1 | 7/2012 | Cook et al. |
| 2014/0287953 A1 | 9/2014 | Gunther et al. |

FOREIGN PATENT DOCUMENTS

WO    WO-2014159696 A1 * 10/2014 ............. A61L 2/208

OTHER PUBLICATIONS

International Search Report and Written Opinion dated Jan. 28, 2016 for Int. Appl. No. PCT/US15/60698, 9 pp.

* cited by examiner

*Primary Examiner* — Jyoti Nagpaul
(74) *Attorney, Agent, or Firm* — James A. Sheridan; Sheridan Law, LLC

(57) ABSTRACT

There is disclosed a system and method for laser cutting of human allograft tissue. One embodiment includes a laser canister having a housing fabricated with a sterilizable material. The housing defines an interior portion, an exterior portion, and a selectively operable opening into the interior portion. The selectively operable opening includes a hermetic seal to maintain a sterile environment from the exterior portion when the selectively operable opening is closed. The canister includes an infrared (IR) transmissive optical window disposed in the housing and configured to allow a laser beam to penetrate therethrough to the interior portion. The canister also includes an insert within the interior portion configured to support human allograft tissue in a sterile environment, the insert being removable from the housing to move the human allograft tissue into another sterile environment after the housing has been exposed to a non-sterile environment. Other embodiments are also disclosed.

14 Claims, 6 Drawing Sheets

ENCLOSURE FOR LASER CUTTING OF HUMAN TISSUE

REFERENCE TO PENDING PRIOR PATENT APPLICATION

This application claims the benefit under 35 U.S.C. 119 (e) of U.S. Provisional Patent Application No. 62/082,755, filed Nov. 21, 2014 by Meghan Gabriel and Raymond Klein for "ENCLOSURE FOR LASER CUTTING OF HUMAN TISSUE," which patent application is hereby incorporated herein by reference.

BACKGROUND

An allograft includes bone, tendon, skin, or other types of tissue that is transplanted from one person to another. Allografts are used in a variety of medical treatments, such as knee replacements, bone grafts, spinal fusions, eye surgery, and skin grafts for the severely burned. Allografts come from voluntarily donated human tissue obtained from donor-derived, living-related, or living-unrelated donors and can help patients regain mobility, restore function, enjoy a better quality of life, and even save lives in the case of cardiovascular tissue or skin.

Allograft processing centers are generally responsible for processing and cataloging allografts collected by organ procurement organizations ("OPOs"). The OPOs are, in turn, responsible for collecting and/or recovering voluntarily donated tissues and gathering any pertinent medical information about those tissues before transferring them to the processing center.

Once an allograft is received, the allograft processing center is then responsible for processing the allograft and readying it for safe and effective medical use. Such processing may involve several steps including inspection, testing, cleansing, and cataloging, all performed in government-certified (or equivalent) laboratories and subject to strict standards and regulations. Allograft tissue is processed to remove all cellular content and remove any risk of infection transmission and tissue rejection. This makes the risk of disease transmission extremely remote. Grafts are sterilized and tissues are carefully preserved in an effort to retain the original structural and biological integrity of the graft. Quality assurance checks are incorporated into the preparation process, including aerobic and anaerobic cultures and any applicable additional testing. Finally, all donor records are reviewed to determine eligibility for transplantation.

Given the careful nature with which allografts are processed and prepared, allograft materials are generally processed in a clean room that provides a sterile environment for the allograft material as well as various processing tools. Tools are introduced into the clean room in a sterilized configuration so as to prevent contamination of the allograft materials already present. Moreover, each clean room is sterilized between donors to prevent cross-contamination from one donor allograft to another donor allograft. Typically, the tools used are sufficiently small and inexpensive as to allow for sterilization and placement in multiple clean rooms, as needed.

Oftentimes, allograft tissue processing requires cutting, etching, and/or engraving. While allograft tissue can be hand cut with conventional cutting tools (e.g., a specialized band saw blade) typically present within the clean room, these cutting tools create additional waste and scrap. For instance, a band saw blade generally destroys allograft material across the width of the blade, which renders undesirable waste.

Laser cutting allograft tissue expedites the cutting process, while reducing the waste and/or scrap created by conventional cutting devices. While laser cutting provides a superior allograft processing alternative, the laser equipment used to cut and/or engrave allograft tissue is generally larger, more intricate, and too expensive to either maintain within each clean room or to sterilize for movement between one clean room and the next. As a result, allograft tissue to be laser cut, etched, and/or engraved must be removed from the clean room and transported to and from centrally located laser equipment without compromising the integrity of the allograft or risking cross-contamination of the tissue to be cut.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides an enclosure device for laser cutting human allograft tissue. The enclosure device includes a housing fabricated with a sterilizable material. The housing defines an interior portion, an exterior portion, and a selectively operable opening into said interior portion, where the selectively operable opening includes a hermetic seal to maintain a sterile environment within the interior portion when the selectively operable opening is closed. The enclosure device also includes an infrared (IR) transmissive optical window disposed in the housing. The IR transmissive optical window is configured to allow a laser beam therethrough to the interior portion. The enclosure further includes an insert within the interior portion, which is configured to support human allograft tissue in the sterile environment, where the insert is removable from the housing to move the human allograft tissue into another sterile environment after the exterior portion of the housing has been exposed to a non-sterile environment.

Another embodiment provides a laser canister for use in cutting human allograft tissue. The laser canister includes a sterilizable housing having a cover portion and a base portion that define an exterior portion and an interior chamber, where the cover portion moves between an open configuration and a closed configuration. When in the open configuration, the interior chamber is configured to receive the allograft tissue in a sterile environment, and when in the closed configuration, the housing is airtight to maintain the sterile environment as the exterior portion is exposed to a non-sterile environment. The laser canister also includes an IR transmissive optical window disposed within the cover portion of the housing. The IR transmissive optical window is positioned to allow a laser beam to penetrate therethrough to contact the allograft tissue within the sterile environment of the interior chamber.

Yet another embodiment provides a method for laser cutting human allograft tissue using a laser canister having a sterilizable housing that defines an exterior portion, an interior chamber, a selectively operable hermetic seal separating the exterior portion from the interior chamber, and an IR transmissive optical window positioned to allow a laser beam to penetrate therethrough into the interior chamber. The method includes (1) loading, within a sterile environment, the allograft tissue into the interior chamber of the housing; (2) activating the selectively operable hermetic seal to separate the interior chamber from the exterior portion of the housing; (3) exposing the housing to a non-sterile environment; (4) using an IR laser directed through the IR transmissive optical window, cutting the allograft tissue; (5) returning the housing to the sterile environment or to another sterile environment; (6) deactivating the selectively operable hermetic seal to connect the interior chamber with the exterior portion of the housing; and (7) aseptically removing the allograft tissue from the interior chamber of the housing.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments of the systems and methods described herein relate to an enclosed but accessible, portable, sterile, and controlled environment for the respective removal and re-introduction of cut, etched, and/or engraved allograft material from and to the sterile processing field of a clean room. One embodiment provides an airtight and autoclaveable canister (which may also be referred to as a container or an enclosure) that utilizes an optical window to allow for laser cutting, etching, and/or engraving of human tissue contained within the canister.

Figure 1:
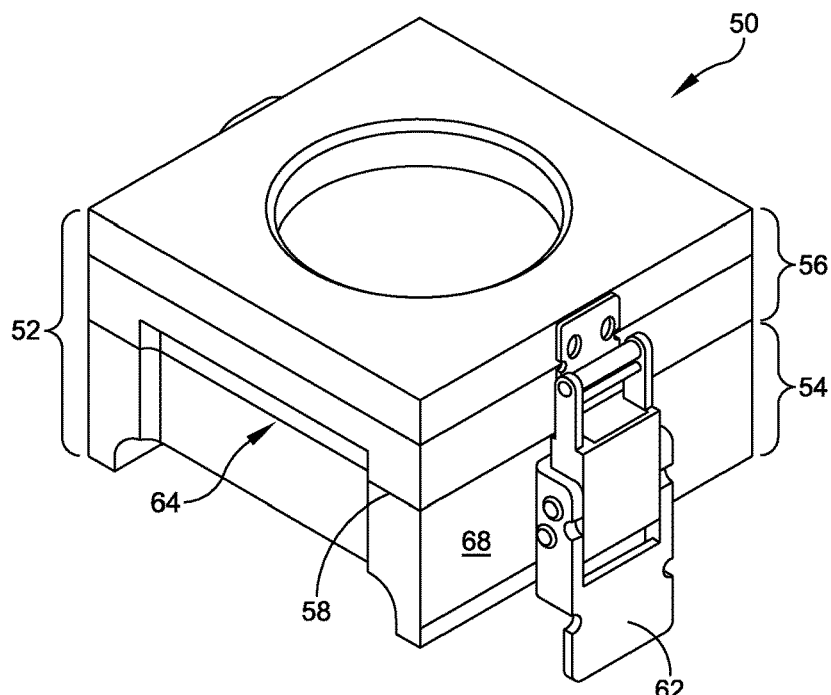
FIG. 1 illustrates a perspective view of one embodiment of a laser-cutting tissue canister having an infrared (IR) transmissive optical window disposed in a cover portion, which is clamped to a base portion to form an airtight seal.

FIG. 1 illustrates a perspective view of one embodiment of an enclosure device or laser canister 50 for use in cutting, etching, and/or engraving human allograft tissue. In this embodiment, canister 50 may include a housing 52 having a base portion 54 disposed beneath a cover portion 56. Base portion 54 and cover portion 56 may meet to define a selectively operable opening 58 into an interior chamber 60, shown in FIG. 2, contained within housing 52. One or more latch components 62 may be attached to housing 50 in a manner that allows cover portion 56 to be removed from base portion 54 along opening 58, thereby facilitating the movement of selectively operable opening 58 within housing 52 between a closed configuration 64, shown in FIG. 1, and an open configuration 66, shown in FIG. 2. Latch components may be formed of stainless steel or any other appropriate material and may take any appropriate size, shape, type, and/or configuration, including, for example, being commercially available drawbolt latches or clamps, with or without hinged features.

When selectively operable opening 58 is in closed configuration 64, base portion 54 and cover portion 56 may meet to form an airtight or hermetic seal between interior chamber 60 and an exterior 68 of housing 52, which is exposed to the ambient environment at the location of canister 50. To achieve this hermetic seal between interior chamber 60 and the ambient environment, one or both of cover portion 56 and base portion 54 may include a groove 69, shown in FIG. 3, designed to retain an o-ring 70, shown in place in FIG. 2. When cover portion 56 and base portion 54 are brought into contact in closed configuration 64 (FIG. 1), o-ring 70 may form an airtight seal between the two components. O-ring 70 may be formed of any appropriate material, including, for example, silicone or rubber.

Figure 4:
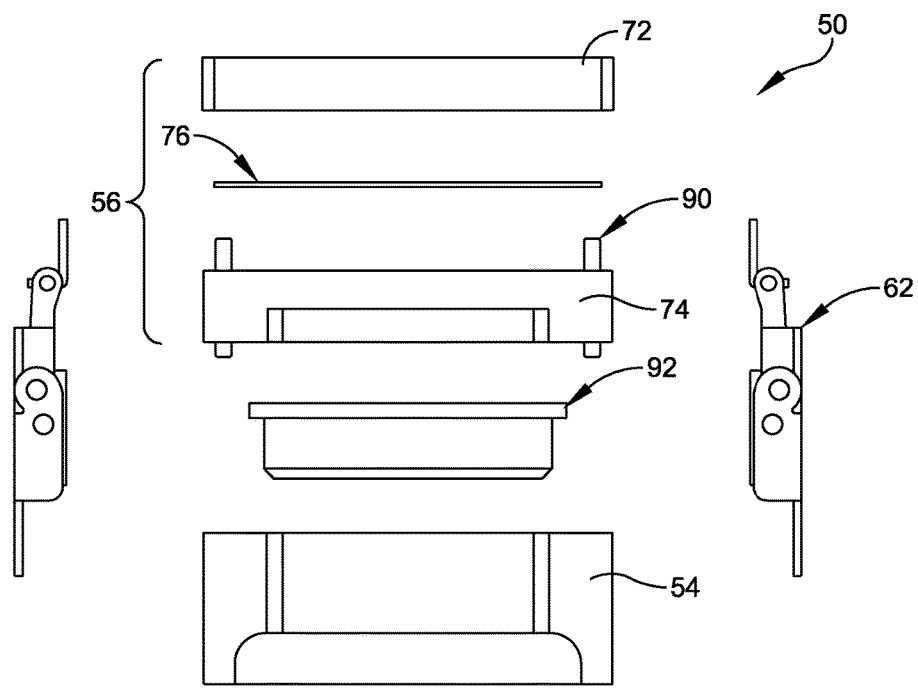
FIG. 4 illustrates an exploded view of the laser-cutting tissue canister of FIG. 1.
Figure 5:
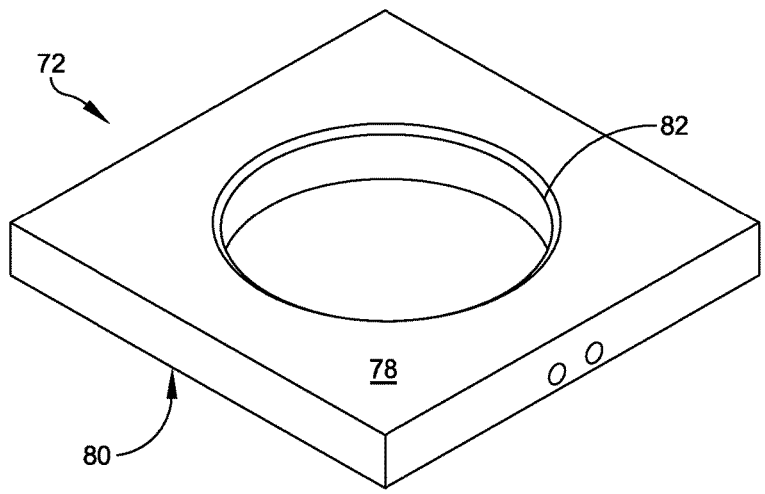
FIG. 5 illustrates a perspective view of one embodiment of a lid for incorporation into the cover portion of the laser-cutting tissue canister of FIG. 1.
Figure 6:
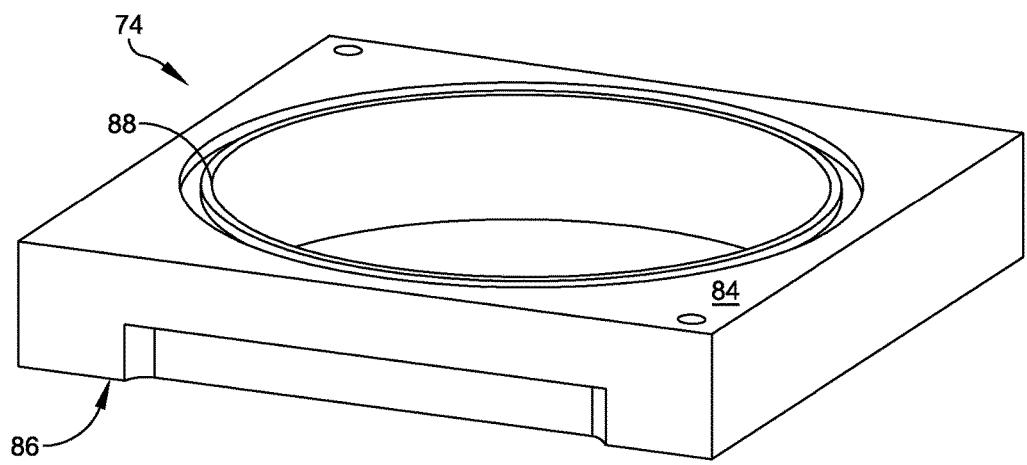
FIG. 6 illustrates a perspective view of one embodiment of a spacer for incorporation into the cover portion of the laser-cutting tissue canister of FIG. 1.
Figure 7:
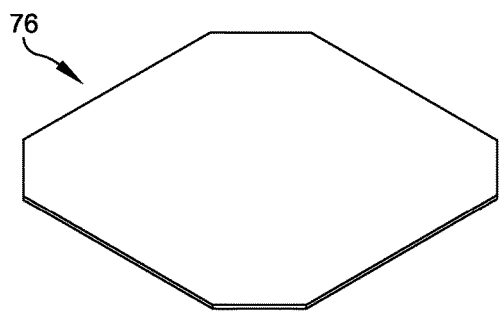
FIG. 7 illustrates a top view of one embodiment of an infrared (IR) transmissive optical window for incorporation into the cover portion of the laser-cutting tissue canister of FIG. 1.

FIG. 4 illustrates an exploded view of laser canister 50, which provides further detail regarding the components that combine to form the canister. In one embodiment, cover portion 56 may be an assembly that includes a lid 72, a spacer 74, and an infrared (IR) transmissive optical window 76, each of which is detailed in FIGS. 5, 6, and 7, respectively. Turning to FIG. 5, lid 72 may have a top surface 78, a bottom surface 80, and a central through-hole 82. FIG. 6 shows that, similarly, spacer 74 may include a top surface 84, a bottom surface 86, and a central through-hole 88. A set of press-fit pins 90 (FIG. 4) may be used to attach lid 72 and spacer 74 in a manner that compresses or face-seals IR transmissive optical window 76 between bottom surface 80 of lid 72 and top surface 84 of spacer 74. Through-holes 82 and 88 may be concentrically aligned, leaving face-sealed IR transmissive optical window 76 exposed in a manner that allows a laser to penetrate therethrough and into interior chamber 60 of housing 52. Embodiments may incorporate one or more additional o-rings to ensure an airtight seal about window 76. In addition, IR transmissive optical window 76 may be formed of any appropriate transparent material that is compatible with the wavelengths of $CO_2$ laser beams, fiber laser beams (e.g., YAG fiber laser beams), and/or other infrared frequencies. By way of limited example, embodiments of window 76 may include material of any of NaCl, ZnSe, Si, Ge, $BaF_2$, $CaF_2$, KBr, or $MgF_2$.

Figure 2:
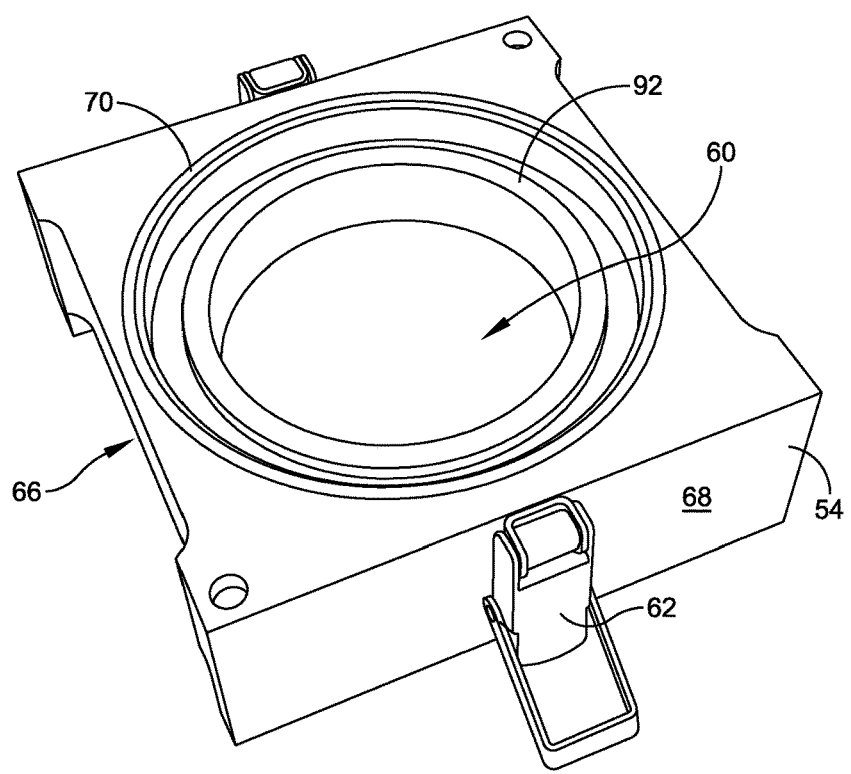
FIG. 2 illustrates a perspective view of one embodiment of the laser-cutting tissue canister of FIG. 1, with the cover portion removed to provide a view of the interior chamber and a removable insert configured to receive allograft tissue.
Figure 3:
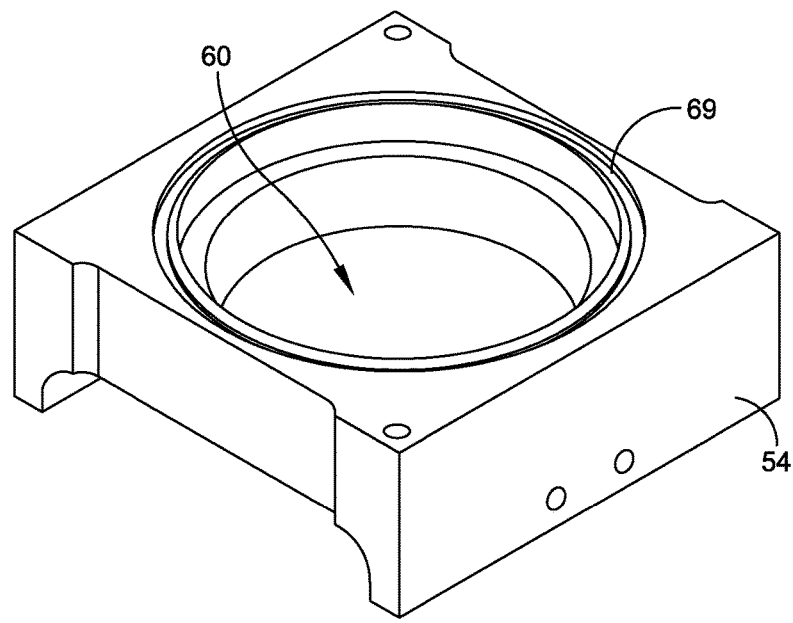
FIG. 3 illustrates a perspective view of one embodiment of the base portion of the laser-cutting tissue canister of FIG. 1, which includes an interior chamber for retaining allograft tissue as well as an o-ring channel for creating a hermetic seal with the cover portion.

The resulting combination of base portion 54 and cover portion 56 yields a hermetically sealed enclosure that utilizes a transparent, laser-penetrable optical window to expose the enclosure's interior to infrared light. Allograft material may be placed within interior chamber 60 of housing 52 when selectively operable opening 58 is in open configuration 66 (FIG. 2). Generally this placement or loading of allograft material may occur in a sterile environment such as a clean room. Once loaded, opening 58 may be moved into closed configuration 64 (FIG. 1), such that an airtight seal separates the loaded allograft material from the ambient environment in contact with exterior 68 of housing 52. Once closed, laser canister 50 may be transported out of the clean room to a different, non-sterile location of a laser-cutting tool, where the laser may be used to pass through IR transmissive optical window 76 and cut, etch, or engrave the allograft material through optical window 76. After this cutting process is complete, laser canister 50 may be transported back into the sterile, clean-room environment and reintroduced to the sterile field before the allograft material is removed for further processing. Thus, allograft material may be laser cut outside the sterile environment without risking exposure of the tissue to the non-sterile environment and/or cross-contamination with the laser chamber.

Figure 8:
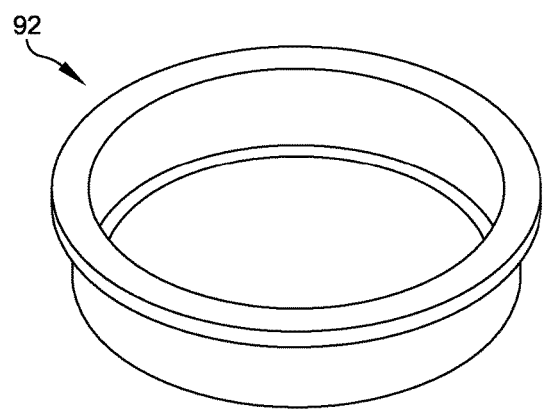
FIG. 8 illustrates a perspective view of one embodiment of a removable insert configured to be nested within the base portion of the laser-cutting tissue canister of FIG. 1 and receive allograft tissue for cutting, etching, and/or engraving.

Returning to FIG. 4, laser canister 50 may also include a removable insert 92. In one embodiment shown in FIGS. 2 and 8, removable insert 92 may be a shallow-walled cup or dish configured to nest within interior chamber 60 of base portion 54. In another embodiment, the insert may incorporate more substantial retaining walls (not shown) that allow for the allograft tissue to remain fully submerged in solution throughout the cutting process. Insert 92 may serve numerous purposes, including facilitating the loading and aseptic removal of allograft material from housing 52. In some embodiments, insert 92 may even be packaged with the allograft material such that insert 92 travels with the tissue throughout the allograft preparation and packaging process.

The components of laser canister 50 may be formed of any appropriate materials (e.g., stainless steel, aluminum, silicon and various o-ring materials) that permit autoclave treatment and other types of sterilization methods such as sterilization by steam and ethylene oxide (EtO) sterilization. Further, the exterior and interior geometric configurations, as well as seal types and seal placements of canister 50 may vary as appropriate to facilitate effective sterilization, decontamination, and sealing of canister 50.

Figure 9:
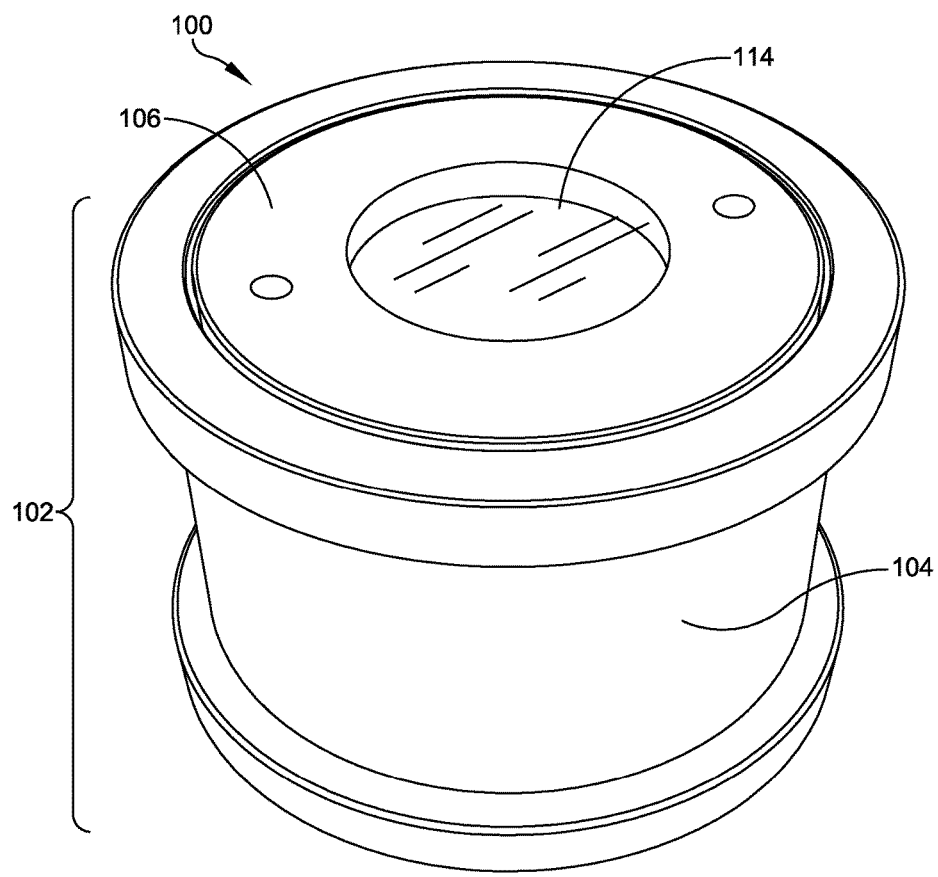
FIG. 9 illustrates a perspective view of another embodiment of a laser-cutting tissue canister having an infrared (IR) transmissive optical window disposed in a cover portion, which attaches via a series of mating threads to a base portion to form a selectively operable hermetic seal.
Figure 10:
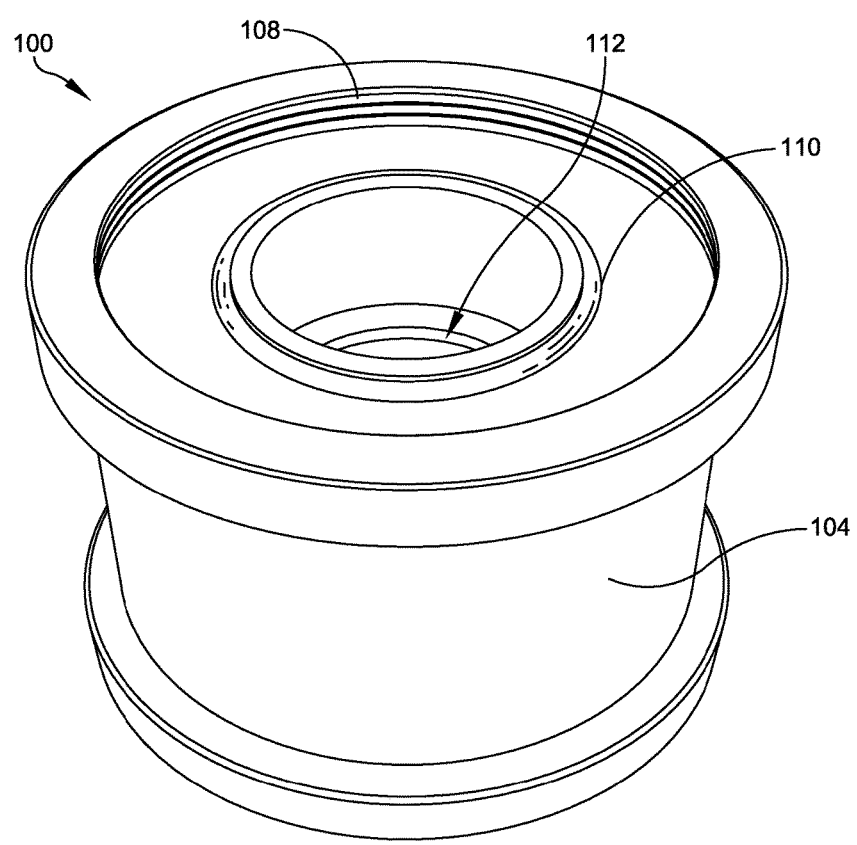
FIG. 10 illustrates a perspective view of one embodiment of the tissue container of FIG. 9, with the cover portion removed to provide a view of an interior chamber configured to receive allograft tissue.

FIGS. 9-10 illustrate perspective views of another embodiment of a laser canister 100 in closed and open configurations, respectively. In this embodiment, canister 100 includes a housing 102 having a round base portion 104 and cover portion 106. Canister 100 functions in the same manner as canister 50, the primary differences being the general shape of the housing and a threaded connection between base portion 104 and lid portion 106. As shown in FIG. 10, base portion 104 may include a set of threads 108 designed to mate with corresponding threads (not shown) on lid portion 106 (FIG. 9). Similar to canister 50 (FIGS. 1-8), canister 100 may incorporate one or more o-rings 110 configured to form a hermetic seal between lid portion 106 and base portion 104, effectively sealing an interior chamber 112 from the external environment when canister 100 is in the closed configuration (FIG. 9). Returning to FIG. 9, lid portion 106 may include an IR transmissive optical window 114, which is compatible with the wavelengths of $CO_2$ laser beams, fiber laser beams (e.g., YAG fiber laser beams), and/or other infrared frequencies to allow a laser beam to penetrate optical window 114 to cut allograft material contained within interior chamber 112 (FIG. 10).

Figure 11:
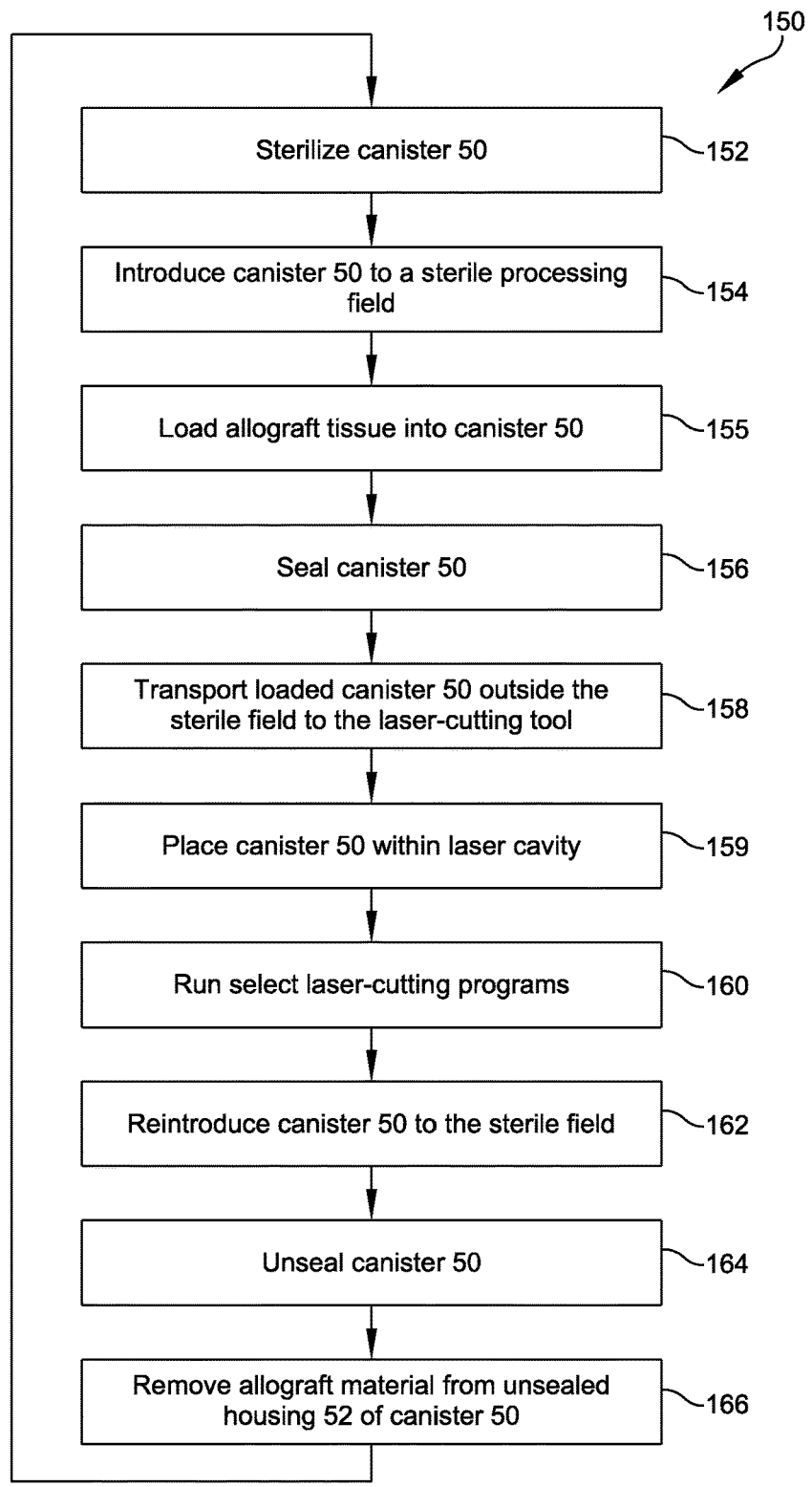
FIG. 11 depicts a flow chart detailing an exemplary method for using the laser-cutting tissue canister of FIGS. 1-2 to laser-cut an allograft tissue sample outside a controlled, sterile environment without risking cross-contamination of the tissue.

FIG. 11 provides a flow chart detailing an exemplary method 150 of using embodiments of an enclosure such as laser canister 50 to laser cut, etch, and/or engrave allograft material. Method 150 begins with the sterilization (152) of the components of canister 50 and the introduction (154) of canister 50 to a sterile processing field such as a clean room where canister 50 may be loaded (155) with allograft tissue to be laser cut, etched, or engraved. The initial steps of sterilizing (152) and introducing (154) canister 50 to the sterile field may occur in any appropriate order depending on the location of the sterilization equipment.

After loading (155) the allograft material, canister 50 may be sealed (156) and transported (158) outside the sterile field and placed within a laser cavity (159), where selected laser-cutting programs may be run (160) to cut, etch, or engrave the allograft material as desired. During this step of running (160) the laser-cutting tool, optical window 76 allows the laser beam to pass into interior chamber 60 of housing 52 to cut the allograft tissue without exposing the tissue to the external environment, thereby allowing the tissue to be cut outside the controlled, sterile field of the clean room without risking cross-contamination. After laser cutting (160) is complete, canister 50 may be reintroduced (162) to the sterile field, and lid 72 may be removed to unseal (164) canister 50 before insert 92 is removed (166) from base 54 of housing 52 to the sterile field for further processing and/or packaging. After method 150 is complete, the process may begin again with the re-sterilization of canister 50 (152) before the placement of another allograft to be cut, engraved, and/or etched.

Beyond allograft materials, canister 50 may be used for the cutting, engraving, and/or etching of any material that requires a controlled environment to limit contamination, though it is not currently contemplated that the canister may be used to cut materials that generate an excessive amount of smoke as that would fill the interior chamber and refract the laser beam, lessening its cutting power.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. An enclosure device for laser cutting human allograft tissue, said enclosure device comprising:
    a housing fabricated with a sterilizable material, said housing defining an interior portion, an exterior portion, and a selectively operable opening into said interior portion, said selectively operable opening including a hermetic seal to maintain a sterile environment within said interior portion when said selectively operable opening is closed;

an infrared (IR) transmissive optical window disposed in said housing, said IR transmissive optical window including a material of at least one of NaCl, ZnSe, Si, Ge, $BaF_2$, $CaF_2$, KBr, and $MgF_2$, said IR transmissive optical window configured to allow a laser beam generated by a laser-cutting tool and configured for laser cutting human allograft tissue therethrough to said interior portion, and said IR transmissive optical window configured to allow the laser beam to pass into the sterile environment of the interior portion to cut the human allograft tissue without exposing the human allograft tissue to the external environment; and an insert within said interior portion, said insert configured to support human allograft tissue in said sterile environment, wherein said insert is removable from said housing to move the human allograft tissue into another sterile environment after said exterior portion of said housing has been exposed to a non-sterile environment.

2. The enclosure device of claim 1, wherein the housing includes a base portion and a cover portion.

3. The enclosure device of claim 2, wherein at least one of said base portion and said cover portion includes an o-ring to provide said hermetic seal of said selectively operable opening.

4. The enclosure device of claim 2, wherein said cover portion includes a lid and a spacer, said spacer having a top surface and a bottom surface in opposition to one another, wherein said top surface is configured to engage with said lid and said bottom surface is configured to engage with said base portion.

5. The enclosure device of claim 2, wherein said selectively operable opening includes at least one latch component selectively attaching said cover portion and said base portion.

6. The enclosure device of claim 2, wherein said selectively operable opening includes a set of alignment pins extending from said cover portion to said base portion.

7. The enclosure device of claim 1, wherein said IR transmissive optical window includes a material compatible with a YAG fiber laser beam.

8. The enclosure device of claim 1, wherein said insert is a dish having a bottom surface and a sidewall extending upwardly from said bottom surface.

9. A laser canister for use in cutting human allograft tissue, comprising:

a sterilizable housing having a cover portion and a base portion that define an exterior portion and an interior chamber, wherein said cover portion moves between an open configuration and a closed configuration, wherein when in said open configuration, said interior chamber is configured to receive the allograft tissue in a sterile environment, and wherein when in said closed configuration, said housing is airtight to maintain said sterile environment as said exterior portion is exposed to a non-sterile environment; and an infrared (IR) transmissive optical window disposed within said cover portion of said housing, said IR transmissive optical window including a material of at least one of NaCl, ZnSe, Si, Ge, $BaF_2$, $CaF_2$, KBr, and $MgF_2$, said IR transmissive optical window positioned to allow a laser beam generated by a laser-cutting tool and configured for laser cutting the allograft tissue to penetrate therethrough to contact the allograft tissue within said sterile environment of said interior chamber, and said IR transmissive optical window configured to allow the laser beam to pass into the sterile environment of the interior chamber to cut the allograft tissue without exposing the allograft tissue to the external environment.

10. The laser canister of claim 9, further comprising an insert disposed within said interior chamber, said insert configured to support the allograft tissue within said sterile environment, wherein said insert is removable from said housing to move the allograft tissue into another sterile environment after said exterior portion is exposed to the non-sterile environment.

11. The laser canister of claim 10, wherein when said cover portion is in said closed configuration, said base portion and said cover portion form a hermetic seal.

12. The laser canister of claim 11, wherein at least one of said base portion and said cover portion includes an o-ring to form said hermetic seal.

13. The laser canister of claim 11, further comprising one or more latch components configured to latch said cover portion in said closed configuration.

14. The laser canister of claim 9, wherein said IR transmissive optical window includes a material compatible with a YAG fiber laser beam.

* * * * *